United States Patent
Shadduck

Patent Number: 6,162,232
Date of Patent: Dec. 19, 2000

[54] INSTRUMENTS AND TECHNIQUES FOR HIGH-VELOCITY FLUID ABRASION OF EPIDERMAL LAYERS WITH SKIN COOLING

[76] Inventor: John H. Shadduck, 1490 Vistazo West St., Tiburon, Calif. 94920

[21] Appl. No.: 09/294,254

[22] Filed: Apr. 19, 1999

Related U.S. Application Data

[60] Provisional application No. 60/125,369, Mar. 18, 1999, and provisional application No. 60/125,399, Mar. 20, 1999.

[51] Int. Cl.[7] .................................................. A61M 1/00
[52] U.S. Cl. ............................ 606/131; 604/289; 604/313
[58] Field of Search ................................... 606/131, 132, 606/159; 604/289, 290, 313, 315

[56] References Cited

U.S. PATENT DOCUMENTS

| | | | |
|---|---|---|---|
| 2,608,032 | 8/1952 | Garver | 51/11 |
| 2,921,585 | 1/1960 | Schumann | 128/355 |
| 3,085,573 | 4/1963 | Meyer et al. | 128/240 |
| 3,476,122 | 11/1969 | Elstein | 606/132 |
| 3,574,239 | 4/1971 | Sollerud | 4/1 |
| 3,715,838 | 2/1973 | Young et al. | 51/12 |
| 4,182,329 | 1/1980 | Smit et al. | 604/23 |
| 4,216,233 | 8/1980 | Stein | 514/757 |
| 4,560,373 | 12/1985 | Sugino et al. | 604/30 |
| 4,646,480 | 3/1987 | Williams | 51/424 |
| 4,676,749 | 6/1987 | Mabille | 433/88 |
| 4,706,676 | 11/1987 | Peck | 600/362 |
| 4,757,814 | 7/1988 | Wang et al. | 128/318 |
| 4,900,316 | 2/1990 | Yamamoto | 602/313 |
| 5,037,432 | 8/1991 | Molinari | 606/131 |
| 5,100,412 | 3/1992 | Rosso | 606/131 |
| 5,207,234 | 5/1993 | Rosso | 128/898 |
| 5,810,842 | 9/1998 | Di Fiore et al. | 606/131 |
| 5,971,999 | 10/1999 | Naldoni | 606/131 |
| 6,024,733 | 2/2000 | Eggers et al. | 604/500 |
| 6,039,745 | 3/2000 | Di Fiore et al. | 606/131 |

FOREIGN PATENT DOCUMENTS

| | | |
|---|---|---|
| 258 901 | 3/1988 | European Pat. Off. . |
| 34 21 390 | 12/1985 | Germany . |
| 234 608 | 4/1986 | Germany . |
| 553076 | 12/1956 | Italy . |
| 1184922 | 10/1987 | Italy . |

*Primary Examiner*—Paul J. Hirsch
*Assistant Examiner*—Michael B. Priddy
*Attorney, Agent, or Firm*—Townsend and Townsend and Crew LLP

[57] ABSTRACT

An instrument and technique for the removal of dermal layers in a controlled manner utilizing (i) a high-pressure gas delivery source, (ii) a source for delivery of a cooling fluid and a crystalline abrasive; and (iii) an aspiration source. The systems together cooperate to jet high-velocity gases and cooling fluids, together with abrasives crystals, against a patient's epidermis to abrade away surface layers in a skin resurfacing treatment. The method of the invention provides a periodic removal of superficial skin layers which enhances the synthesis of dermal collagen aggregates by inducing the body's natural wound healing response. The method of the invention creates more normal dermal architectures in skin with limited depths of skin removal by the series of superficial treatments that may be comparable to the extent of collagen synthesis caused by a deeper skin removal treatments such as $CO_2$ laser skin removal.

32 Claims, 10 Drawing Sheets

INSTRUMENTS AND TECHNIQUES FOR HIGH-VELOCITY FLUID ABRASION OF EPIDERMAL LAYERS WITH SKIN COOLING

CROSS-REFERENCE TO RELATED APPLICATIONS

This application is related to Provisional U.S. patent application Ser. No. 60/125,369 filed Mar. 18, 1999 titled Skin Resurfacing Technique and Instrument for Air-Assisted Chemical Etching of Dermal Layers. This application also is related to U.S. patent application Ser. No. 09/271,610 filed Mar. 17, 1999 titled Technique and System for Controlled Chemically-Mediated Removal of Skin Layers; U.S. patent application Ser. No. 09/210,293 filed Dec. 11, 1998 titled Surgical Instrument for High Pressure Fluid Debridement of Epithelial Layers, and Provisional U.S. patent application Ser. No. 60/125,399 filed Mar. 20, 1999 titled High-Pressure Water Jet Abrasive Technique and Instrument for Skin Resurfacing. All of the above listed applications are incorporated herein in their entirety by these references.

BACKGROUND OF THE INVENTION

1. Field of the Invention

The present invention relates to devices for dermatology and more particularly to a hand-held instrument together with (i) a high-pressure gas delivery source, (ii) a source for delivery of a cooling fluid and a crystalline abrasive; and (iii) an aspiration system, which systems together cooperate to jet high-velocity gases and cooling fluids together with abrasives crystals against a patient's epidermis to abrade away surface layers for therapeutic purposes, as well to capture and remove tissue debris from the patient's skin in a closed system.

2. Description of Background Art

Dermatologists and plastic surgeons have used various methods for removing superficial skin layers skin to cause the growth of new skin layers (i.e., commonly described as skin resurfacing techniques) since the early 1900's. Early skin resurfacing treatments used an acid such as phenol to etch away surface layers of a patient's skin that contained damage to thereafter be replaced by new skin. (The term damage when referring to a skin disorder is herein defined as any cutaneous defect, e.g., including but not limited to rhytides, hyperpigmentation, acne scars, solar elastosis, other dyschromias, stria distensae, seborrheic dermatitus).

Figure 1A:
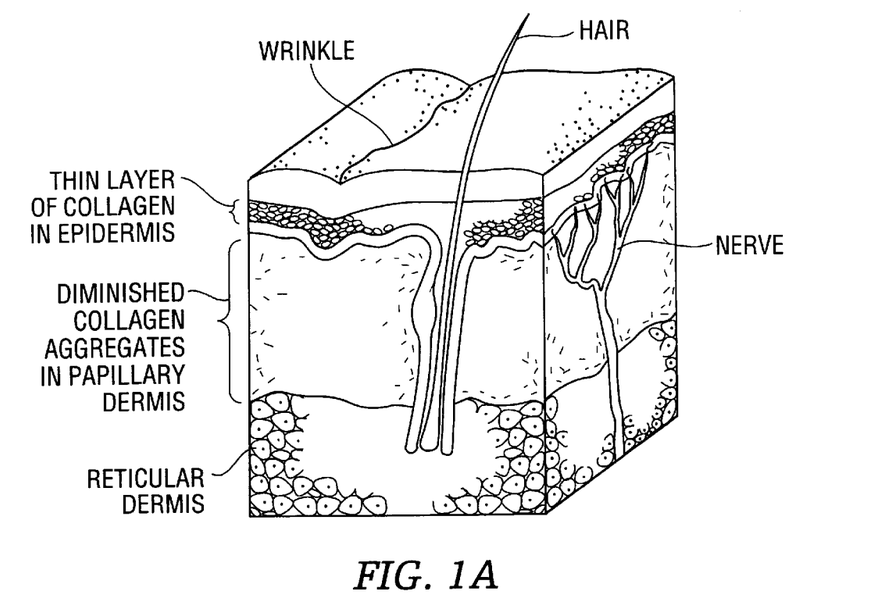
FIGS. 1A—1A are sectional illustrations of a patient's skin showing dermal layers.
Figure 1B:
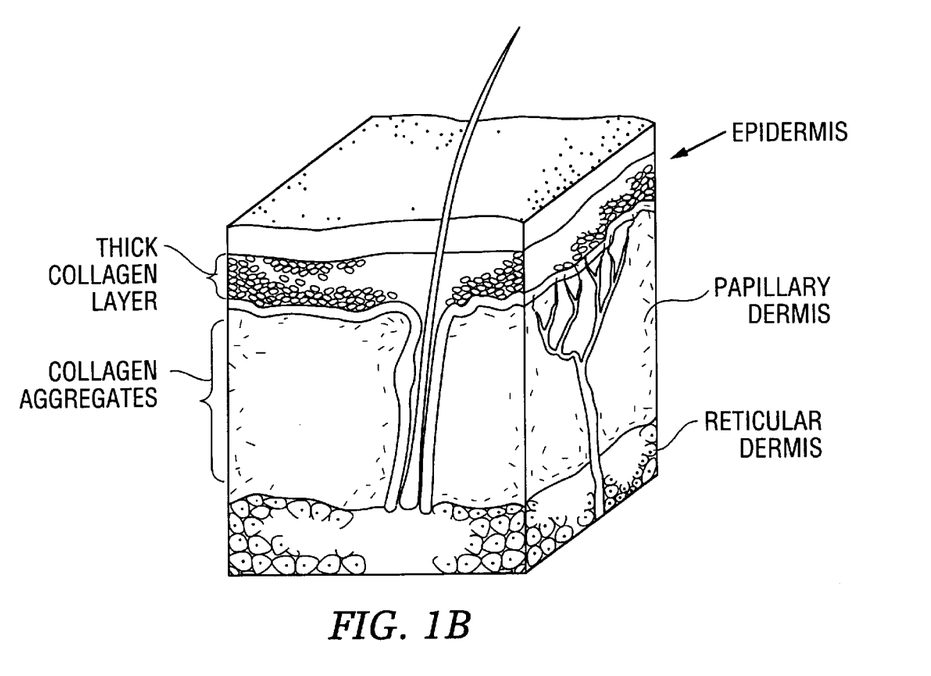

Following the removal of surface skin layer, no matter the method of skin removal, the boy's natural wound-healing response begins to regenerate the epidermis and underlying wounded skin layers. The new skin layer will then cytologically and architecturally resemble a younger and more normal skin. The range of resurfacing treatments can be divided generally into three categories based on the depth of the skin removal and wound: (i) superficial exfoliations or peels extending into the epidermis, (ii) medium-depth resurfacing treatments extending into the papillary dermis, and (iii) deep resurfacing treatments that remove tissue to the depth of the reticular dermis (see FIGS. 1A–1B).

Modern techniques for skin layer removal include: $CO_2$ laser resurfacing which falls into the category of a deep resurfacing treatment; Erbium laser resurfacing which generally is considered a medium-depth treatment; mechanical dermabrasion using high-speed abrasive wheels which results in a medium-depth or deep resurfacing treatment; and chemical peels which may range from a superficial to a deep resurfacing treatment, depending on the treatment parameters. A recent treatment, general called microdermabrasion, has been developed that uses an air-pressure source to deliver abrasive particles against a patient's skin to abrade away skin layers. Micro-dermabrasion as currently practiced falls into the category of a superficial resurfacing treatment.

A superficial exfoliation, peel or abrasion removes some or all of the epidermis (see FIGS. 1A–1B) and thus is suited for treating very light rhytides. Such a superficial exfoliation is not effective in treating many forms of damage to skin. A medium-depth resurfacing treatment that extends into the papillary dermis (see FIG. 1B) can treat many types of damage to skin. Deep resurfacing treatments, such as $CO_2$ laser treatments, that extend well into the reticular dermis (see FIG. 1B) causes the most significant growth of new skin layers but carry the risk of scarring unless carefully controlled.

It is useful to briefly explain the body's mechanism of resurfacing skin in response to removal of dermal layers. Each of the above-listed depths of treatment disrupts the epidermal barrier, or a deeper dermal barrier (papillary or reticular), which initiates varied levels of the body's wound-healing response. A superficial skin layer removal typically causes a limited wound-healing response, including a transient inflammatory response and limited collagen synthesis within the dermis. In a medium-depth or a deep treatment, the initial inflammatory stage leads to hemostasis through an activated coagulation cascade. Chemotactic factors and fibrin lysis products cause neutrophils and monocytes to appear at the site of the wound. The neutrophils sterilize the wound site and the monocytes convert to macrophages and elaborate growth factors which initiate the next phase of the body's wound-healing response involving granular tissue formation. In this phase, fibroblasts generate a new extracellular matrix, particularly in the papillary and reticuilar dermis, which is sustained by angiogenesis and protected anteriorly by the reforming epithelial layer. The new excellular matrix is largely composed of collagen fibers (particularly Types I and III) which are laid down in compact parallel arrays (see FIG. 1B). It is largely the collagen fibers that provide the structural integrity of the new skin—and contribute to the appearance of youthful skin.

All of the prevalent types of skin damage (rhytides, solar elastosis effects, hyperpigmentation, acne scars, dyschromias, melasma, stria distensae) manifest common histologic and ultrastructural characteristics, which in particular include disorganized and thinner collagen aggregates, abnormalities in elastic fibers, and abnormal fibroblasts, melanocytes and keratinocytes that disrupt the normal "architecture" of the dermal layers. It is well recognized that there will be a clinical improvement in the condition and appearance of a patient's skin when a more normal architecture is regenerated by the body's wound-healing response. Of most significance to a clinical improvement is skin is the creation of more dense parallel collagen aggregates with decreased periodicity (spacing between fibrils). The body's wound-healing response is responsible for synthesis of these collagen aggregates. In addition to the body's natural wound healing response, adjunct pharmaceutical treatments that are administered concurrent with, or following, a skin exfoliations can enhance the development of collagen aggregates to provide a more normal dermal architecture in the skin—the result being a more youthful appearing skin.

The deeper skin resurfacing treatments, such as laser ablation, chemical peels and mechanical dermabrasion have drawbacks. The treatments are best used for treatments of a patient's face and may not be suited for treating other portions of a patient's body. For example, laser resurfacing of a patient's neck or décolletage may result in post-treatment pigmentation disorders. All the deep resurfacing treatments are expensive, require anesthetics, and must be performed in a clinical setting. Perhaps, the most significant disadvantage to deep resurfacing treatments relates to the post-treatment recovery period. It may require up to several weeks or even months to fully recover and to allow the skin the form a new epidermal layer. During a period ranging from a few weeks to several weeks after a deep resurfacing treatment, the patient typically must wear heavy make-up to cover redness thus making the treatment acceptable only to women.

The superficial treatment offered by micro-dermabrasion has the advantages of being performed without anesthetics and requiring no extended post-treatment recovery period. However, micro-dermabrasion as currently practices also has several disadvantages. First, a micro-dermabrasion treatment is adapted only for a superficial exfoliation of a patient's epidermis which does not treat many forms of damage to skin. Further, the current micro-dermabrasion devices cause abrasive effects in a focused area of the skin that is very small, for example a few $mm.^2$, since all current devices use a single pin-hole orifice that jets air and abrasives to strike the skin in a highly focused area. Such a focused treatment area is suitable for superficial exfoliations when the working end of the device is passed over the skin in overlapping paths. However, such focused energy delivery is not well suited for deeper skin removal where repeated passes may be necessary. Additionally, current micro-dermabrasion devices are not suited for deeper skin removal due to the pain associated with deep abrasions. Another disadvantage of the current micro-dermabrasion devices is that the aluminum oxide abrasive particles that are typically used contaminate the environment thus creating a health hazard for operators and patients alike. Inhalation of aluminum oxide particles over time can result in serious respiratory disorders.

SUMMARY AND ADVANTAGES OF THE INVENTION

In general, the system of the present invention provides a technique for controlled removal of skin layers to a superficial depth, or slightly deeper, in a patient's dermis as depths are defined above. The skin removal is accomplished by using a crystalline abrasive media that intermixes in the working end of a hand-held device with a plurality of high-velocity gas streams. The treatment is adapted to be used in a periodic therapy to enhance the synthesis of dermal collagen aggregates by inducing the body's natural wound healing response. Thus, it is an objective of the invention to create more normal dermal architectures in skin with lesser depths of skin removal by a series of deep superficial treatments. By removing a superficial layer of skin (or to a medium depth), it is believed that layers of collagen aggregates can be created that may be comparable to the extent of collagen synthesis caused by a single deep skin removal treatment (e.g., $CO_2$ laser skin removal). In other words, the treatments proposed herein may attain the effects of deeper treatments without the undesirable side effects. Most important, the patient would not have to endure any post-treatment recovery times, since each superficial abrasive treatment will only cause transient redness.

The invention also provides a skin cooling system that provides a substantially atomized liquid flow into the working end of the device to contact the skin during a treatment which reduces apparent pain sensation to the patient. This aspect of the technique means that aestheticians may typically perform the proposed treatments and that anesthetics should not be required.

More in particular, the present invention provides a hand-held body having a working end that carries means for media delivery therein, including (i) a high-pressure gas delivery source connected to a plurality of ducts in the working end to create a plurality of gas jets to strike the skin, (ii) a source for delivery of a cooling fluid that carries a crystalline abrasive through a bore in the working end; and (iii) an aspiration source for capturing and removing tissue debris from the patient's skin through an interior chamber of the working end.

The instrument system further provides a hand-held body that carries a de-matable duct component that may be configured with variously dimensioned ducts for introducing media into the interior chamber of the working end of the device to provide varied treatment parameters. The system includes a computer controller that controls media flows from the various sources or reservoirs (the term media or fluid are used to describe any composition capable of flowing, i.e., a liquid or a gas). The system has cooperating $1^{st}$ and $2^{nd}$ delivery means: the $1^{st}$ delivery means comprising a gas source for introducing high-pressure gas streams into the interior chamber and over the patient's skin that is partly received by an open end of the working end; and, the $2^{nd}$ delivery means comprising a source for introducing a crystalline abrasive-carrying cooling fluid into the interior chamber under very low pressure, or no pressure, to intermix with the high-pressure gas streams.

The system's use of a very low pressure liquid agent to carry crystal abrasives offers several advantages: First, the liquid is atomized by the gas streams and sprayed against the epidermis during the crystalline abrasion process to reduce or eliminate the patient's sensation of pain. Pain reduction occurs, it is believed, principally by the liquid absorbing and conducting heat away from the skin. This reduction of pain allows to use of higher velocity gas streams and finer crystalline abrasives to provide a finer dermabrasion. Without the cooling liquid, such a treatment modality would exceed the patient's pain threshold. Further, the use of low-pressure fluid delivery of abrasive crystals allows for the abrupt termination of the fluid flow thus preventing abrasive crystals from flowing into the operating environment after the device is lifted away from the patient's skin. Still further, the crystalline abrasive will combine and attach to the atomized water droplets after striking the skin thus allowing the spent crystals to be easily collected by the aspiration system of the invention. The use of a coolant fluid to carry a selected crystalline agent allows very fine crystalline substances (e.g., aluminum oxide) to be used safely. The invention may be use with crystals ranging is size from about 1 $\mu$m to about 30 $\mu$m in maximum cross-sectional dimension, and preferably in range of about 5 $\mu$m to about 15 $\mu$m in maximum cross-section. The use of such crystals provides a very fine abrasion of the epidermis which would not be possible with currently available devices. Such fine crystals would cause excessive pain to the patient without the cooling system of the invention. More important, such fine crystals would cause a more significant health hazard if inhaled by the patient or operator. The system's use of spent cooling fluid to adhere to the crystals provides for collection of substantially all spent crystals to prevent contamination of the operating environment.

It is an advantage of this invention to provide means for reducing the sensation of pain in a dermabrasion treatment by cooling the treatment area with an atomized liquid.

It is a further advantage of this invention to provide cooling means for reducing pain rather than resorting to anesthetic agents.

It is an advantage of this invention to provide a technique for inducing the synthesis of collagen aggregates in the dermis to reduce the depth and appearance of wrinkles without removing skin to the depth of the reticular dermis.

It is an advantage of this invention to provide a technique for periodic removal of layers of the epidermis to induce the synthesis of collagen to create substantially thick collagen aggregates in the dermis to reduce the depth and appearance of wrinkles.

It is a further advantage of this invention to provide a system that collects and aspirates substantially all spent abrasive particles from the treatment area to prevent inhalation by the patient or system operator.

It is a further advantage of this invention to provide a system that collects and aspirates skin detritus from the treatment area to prevent biological contamination of the environment.

It is a further advantage of this invention to provide a system that can safely use very fine abrasive crystals ranging from about 1 $\mu$m to about 15 $\mu$m in maximum cross section to create a very fine abrasive effect.

It is a further advantage of this invention to provide a skin abrasion system that cause high-velocity flows to strike the skin over a wide path with an even energy distribution.

It is a further advantage of this invention to provide a system that has an independent source for introducing crystalline abrasive into high-velocity gas flows to allow independent modulation of fluid flow parameters.

It is a further advantage of this invention to provide a computer controller to control and modulate the introduction and termination fluid flows into the working end, as well as aspiration power settings, to insure optimal abrasion effects and the capture of spent fluids.

It is a further advantage of this invention to provide a device with a working end that is scalable to allow the treatment area of a patient's skin to be very small or and very large.

It is a further advantage of this invention to provide a system for resurfacing skin that does not require any post-treatment recovery period by providing a series of periodic treatments.

It is a further advantage of this invention to provide a skin resurfacing method that does not require post-treatment use of cosmetic make-up thus making the procedure available to men.

Other advantages and features of the invention will readily become apparent from the following detailed description of the invention and the embodiments thereof, from the claims and the accompanying drawings.

BRIEF DESCRIPTION OF THE DRAWINGS

FIGS. 9A–9B are views showing the manner of using the working end of the invention to perform a method of the invention.

DETAILED DESCRIPTION OF THE INVENTION

1. Type "A" Cooling Fluid/Abrasive Skin Resurfacing System.

Figure 2A:
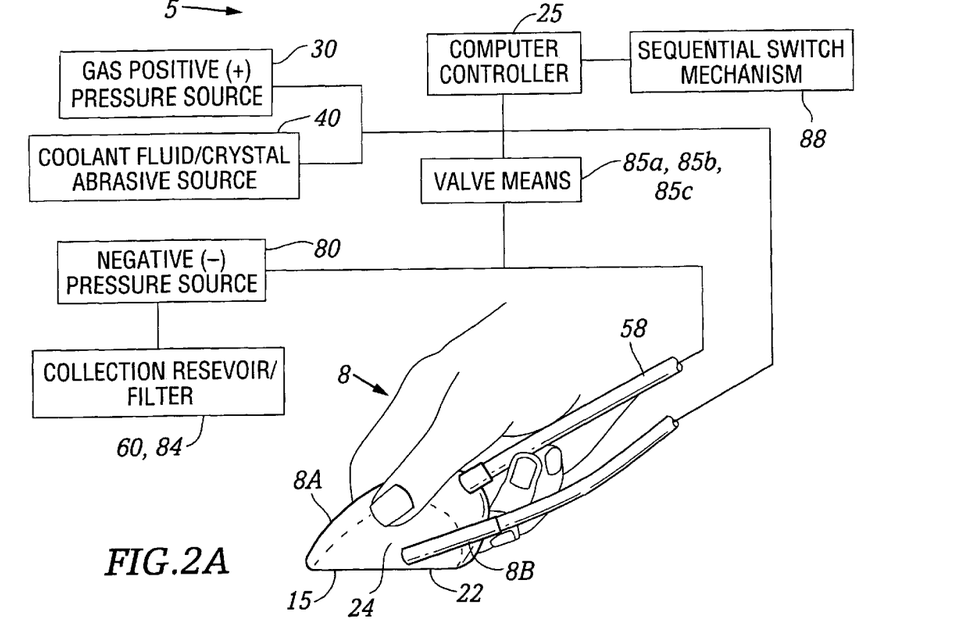
FIGS. 2A–2B are views of different sizes of Type "A" handpiece bodies of the present invention.
Figure 2B:
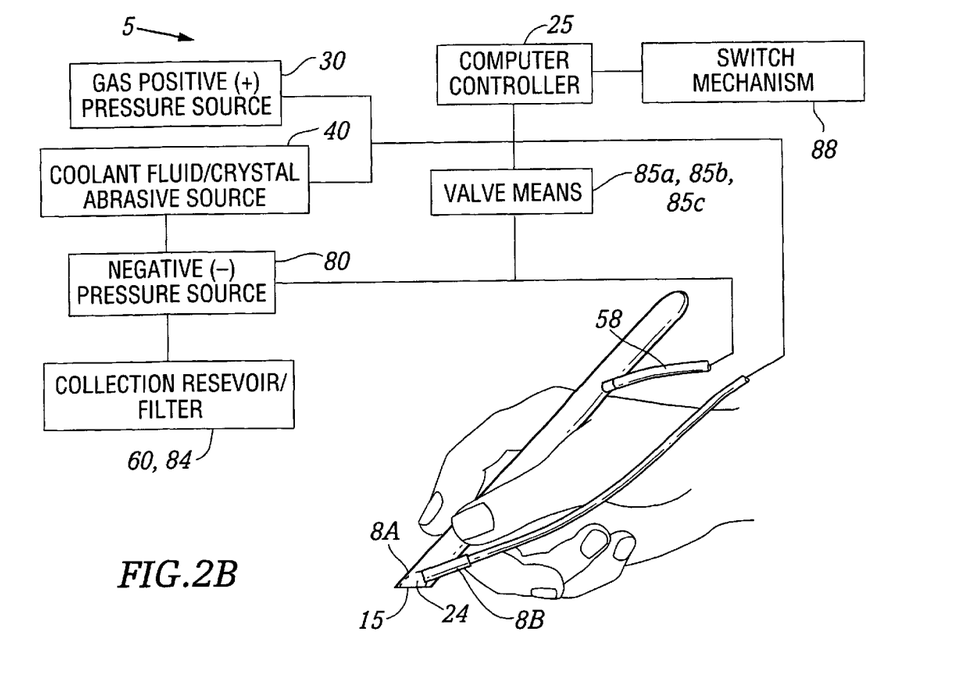

Referring to FIGS. 2A–2B, an exemplary instrument system 5 is shown that is adapted for removal of superficial skin layers. The instrument system 5 includes: (i) a hand-held body 8 (comprising first and second body components 8A and 8B) having a skin interface surface indicated at 15 with an opening portion 22 that extends to interior chamber portion 24 to interface with a treatment area TA of a patient's skin, and (ii) delivery means for introducing (A) high-pressure gas streams and (B) cooling/abrasive fluid flows to the working end of the body 8 together with (C) vacuum means for aspirating skin debris from the targeted treatment area TA.

As can be seen in FIGS. 2A–2B, the instrument system 5 includes a computer controller 25 that controls media flows from the various sources or reservoirs (the term media is used interchangeably herein with the term fluid, and is defined as any composition that is capable of flowing, i.e., a liquid or a gas, and that is used to strike the skin and assist in the exfoliation of skin layers). A $1^{st}$ delivery means comprising a gas source or reservoir indicated at 30 is provided to introduce high-pressure media flows through duct component SB to develop high-pressure gas streams 36A and 36B in interior chamber (see FIGS. 3A–3B and FIG. 4). A $2^{nd}$ delivery means comprising a media reservoir or source indicated at 40 is provided to introduce a cooling fluid CF carrying crystal abrasives CA into interior chamber 24 to intermix with the high-pressure gas streams 36A and 36B.

Figure 4:
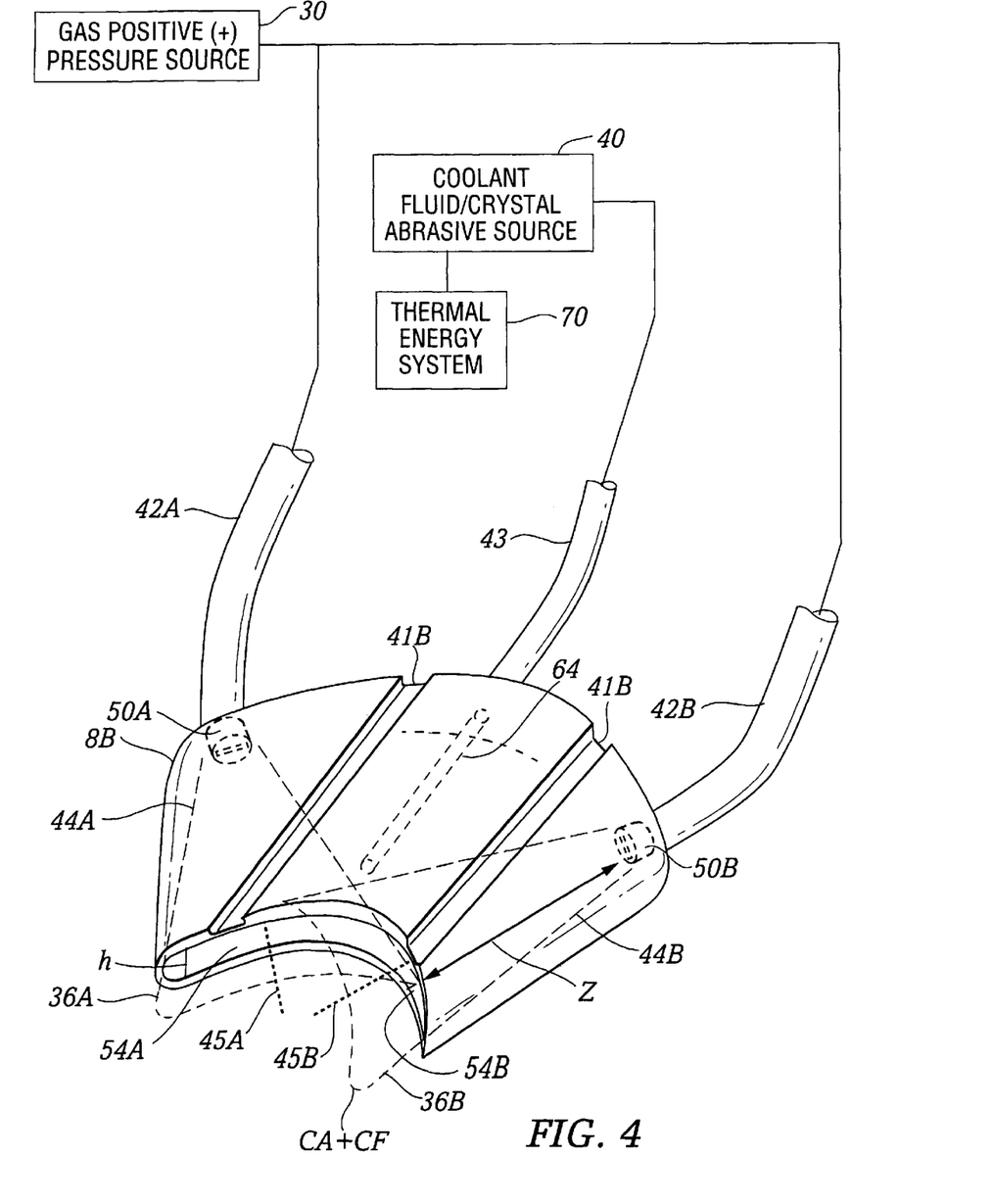
FIG. 4 is perspective view of a duct component of either body of FIGS. 3A–3B.

This invention offers several advantages by using an independent low-pressure $2^{nd}$ delivery means 40 for introducing the abrasive-carrying media into interior chamber 24 under very low pressures, or the absence of pressure. The advantages follow: First, it has been found that delivery of a liquid against the epidermis during micro-dermabrasion reduces the patient's sensation of pain. It is believed the reduction in pain is caused mostly by the liquid absorbing and conducting heat away from the treatment area TA. This factor allows the system to use higher velocity gas streams and finer crystalline abrasives to provide a very fine dermabrasion treatment that would far exceed the patient's pain threshold without the use of a cooling fluid. Second, the use of low-pressure introduction (or no pressure introduction as described below) of crystal abrasives CA in a fluid (fluid being defined as flowable medium, i.e., liquid or gas) allows such a fluid flow to be terminated abruptly to prevent abrasive crystals from flowing into the operating environment after the working (skin-interface) surface 15 is lifted away from the patient's skin. Third, the use of an crystalline abrasive-laden fluid, such as sterile water, allows the water to essentially atomize into water droplets as it intermixes with the high-velocity gas streams 36A–36B to allow the abrasive crystals to strike and abrade the skin (FIG. 4). Thereafter, the water mist substantially attaches to the spent crystals in the interior chamber 24 to make the spent crystals more easily collectable by the aspiration system (described below). By this means, the spent crystals will be entirely collected and will not contaminate the operating environment. Both the last two advantages offer substantial advantages over current systems which create a substantial health hazard by contaminating the operating environment with aluminum oxide crystals or other similar abrasive particles.

Returning now to FIGS. 2A–2B, the body 8 of the invention is scalable to various sizes to provide different treatment dimensions by providing a smaller or larger open portion 22, for example in the exemplary bodies 8 shown in FIGS. 2A–2B. The body 8 of FIG. 2A is of a large size for gripping between the fingers of the operator or in the palm of the operator. The body 8 of FIG. 2B is of a smaller size for a pen-like grip between the operator's fingers.

Figure 3A:
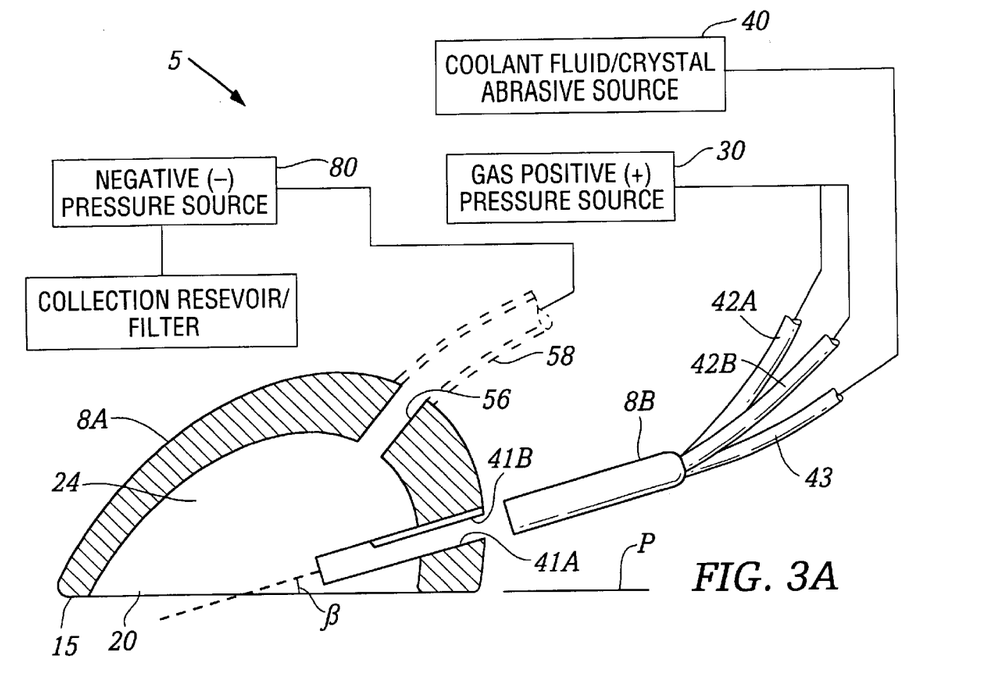
FIGS. 3A–3B are enlarged sectional views of the handpiece bodies of FIGS. 2A–2B take along lines 3A—3A and 3B—3B rotated 90°.
Figure 3B:
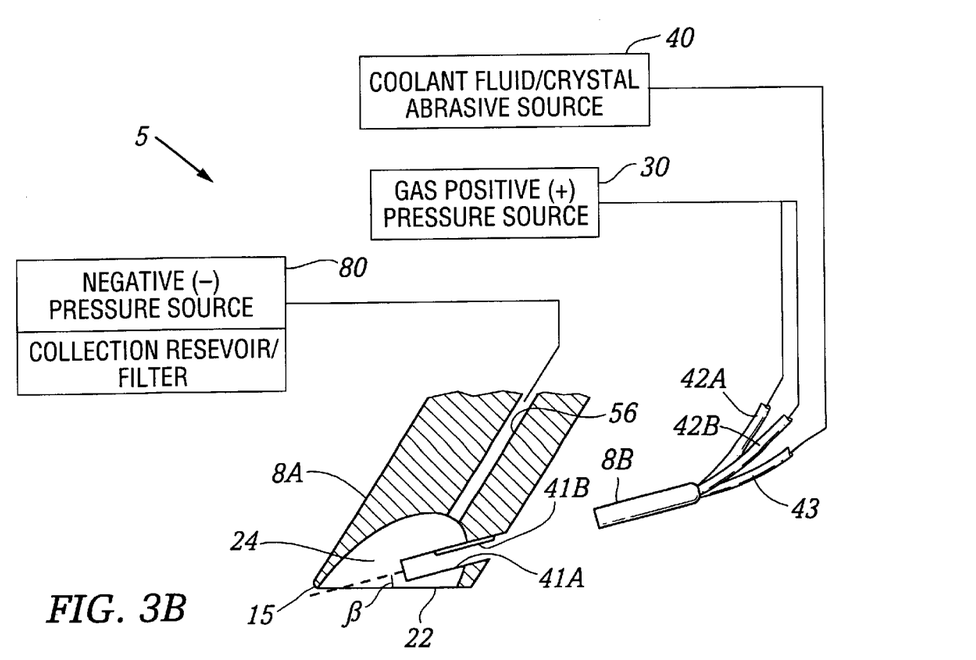

Of particular interest, the exemplary embodiments of FIGS. 2A–2B are provided with first and second de-matable body components 8A and 8B, which are illustrated in FIGS. 3A–3B. The (first) tissue-interface body component is indicated at 8A. The (second) fluid-flow duct component is indicated at 8B and is adapted to slidably fit into a cooperating receiving slot 41A in tissue-interface body 8A with cooperating keyways 41B in the bodies 8A and 8B adapted to align the components. FIG. 4 is a perspective view an exemplary duct component 8B which shows flexible gas supply tubing 42a–42b attached thereto as well as cooling fluid tubing 43. The advantages of providing a de-matable duct component 8B are several which include the following: (i) various duct components 8B may be configured with particular duct dimensions for accelerating gas flows therethrough or for laterally-distributing gas streams to optimize various skin treatment parameters, and the de-matable aspect of component 8B allows it to be switched out quickly from a cooperating body component 8A; (ii) a duct component 8B that is de-matable may be injection molded in an inexpensive manner and may be disposable along with the supply tubing; (iii) a duct component 8B in some applications may require cleaning and the disclosed de-matable component 8B facilitates its switching out for cleaning or replacement; and (iv) a particular duct component 8B may switched between different side-interface bodies 8A to select an optimal angle-of-attack of high-pressure gas streams against the skin (described further below) which is determined by body 8A.

Figure 5A:
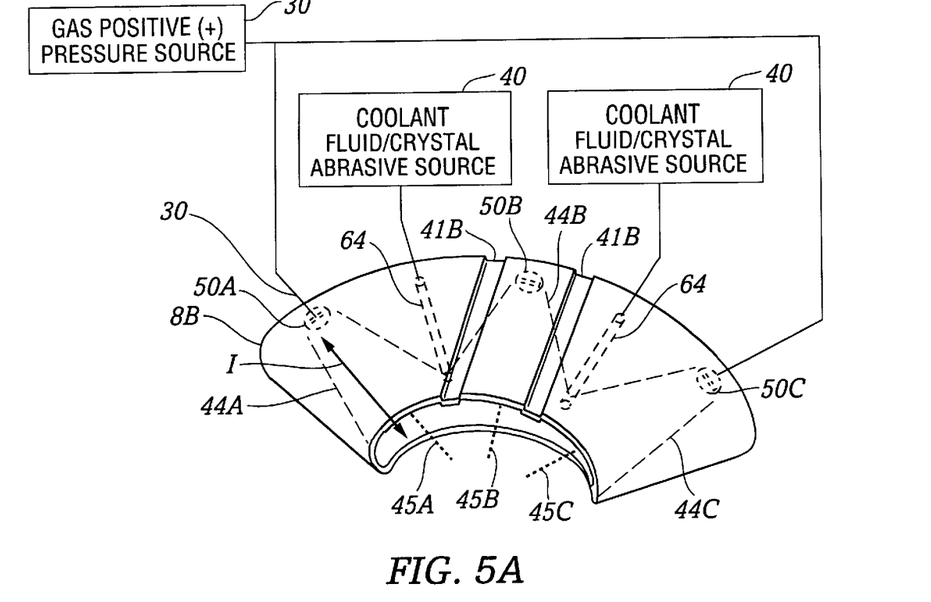
FIGS. 5A–5B are views of alternative embodiments of the duct component of FIG. 4.
Figure 5B:
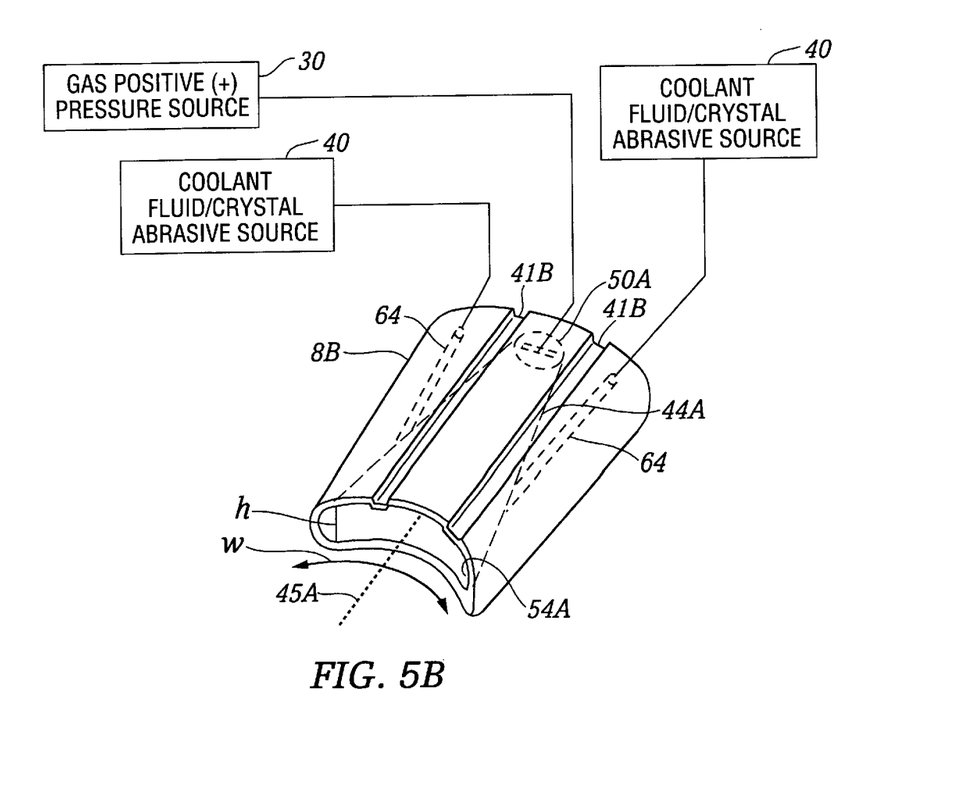
Figure 6A:
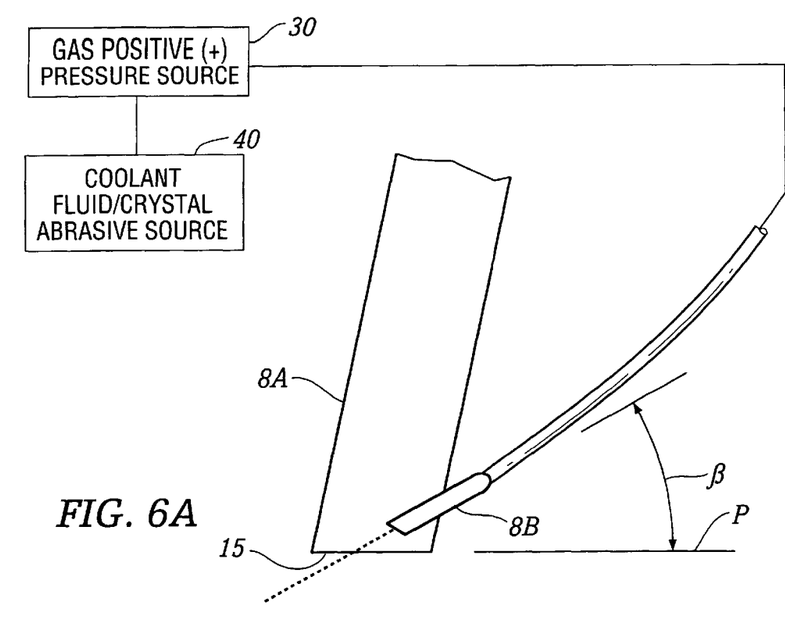
FIGS. 6A–6B are views of alternative embodiments of a handpiece similar to that shown in FIG. 2B.
Figure 6B:
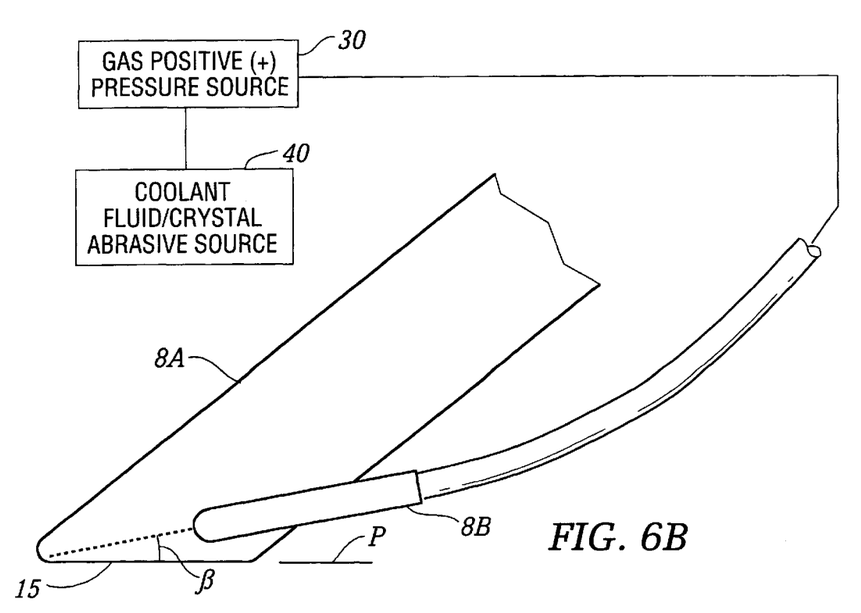

FIGS. 4 & 5A–5B show alternative duct-carrying components 8B that are configured with one or more of flow ducts 44a–44c, with each duct defining a corresponding flow axis 45a–45c, with duct dimensions and parameters that are described in detail below. FIGS. 5A–8B show that multiple coolant inflow passageways fall within the scope of the invention. FIGS. 6A–6B show alternative skin-interface bodies 8A with variously angled surfaces 15, each example of which has a receiving slot 41A that is adapted to receive any particular duct component 8B, for instance any of the exemplary components 8B of FIGS. 4 & 5A–5B. As can be seen in FIGS. 3A–3B and FIGS. 6A–6B, the skin interface surface 15 about open portion 22 defines a particular angle-of-attack β of high-velocity gas streams against the surface of the skin, which generally is the angle of slot 41A relative to skin interface surface 15. Of particular interest, it has been found that lower angles-of-attack of fluid and/or agent flows against the skin causes less sensation of pain than higher angles-of attack, and that various areas of skin on a patient's body (as well as various skin types) have differing pain thresholds. Also, it has been found that higher flow velocities are permitted at lower angles-of-attack for a given level of pain sensation. Therefore, the bodies 8A can be configured with a receiving slot 41A at a selected angle β to optimize the angle-of-attack via fluid flow ducts 44a–44c and about fluid flow axes 45a–45c. A preferred embodiment of the body 8 defines angle β within a range from about 0 to 40°. More preferably, the body 8 defines angle β within a range from about 5° to 25°.

Figure 7:
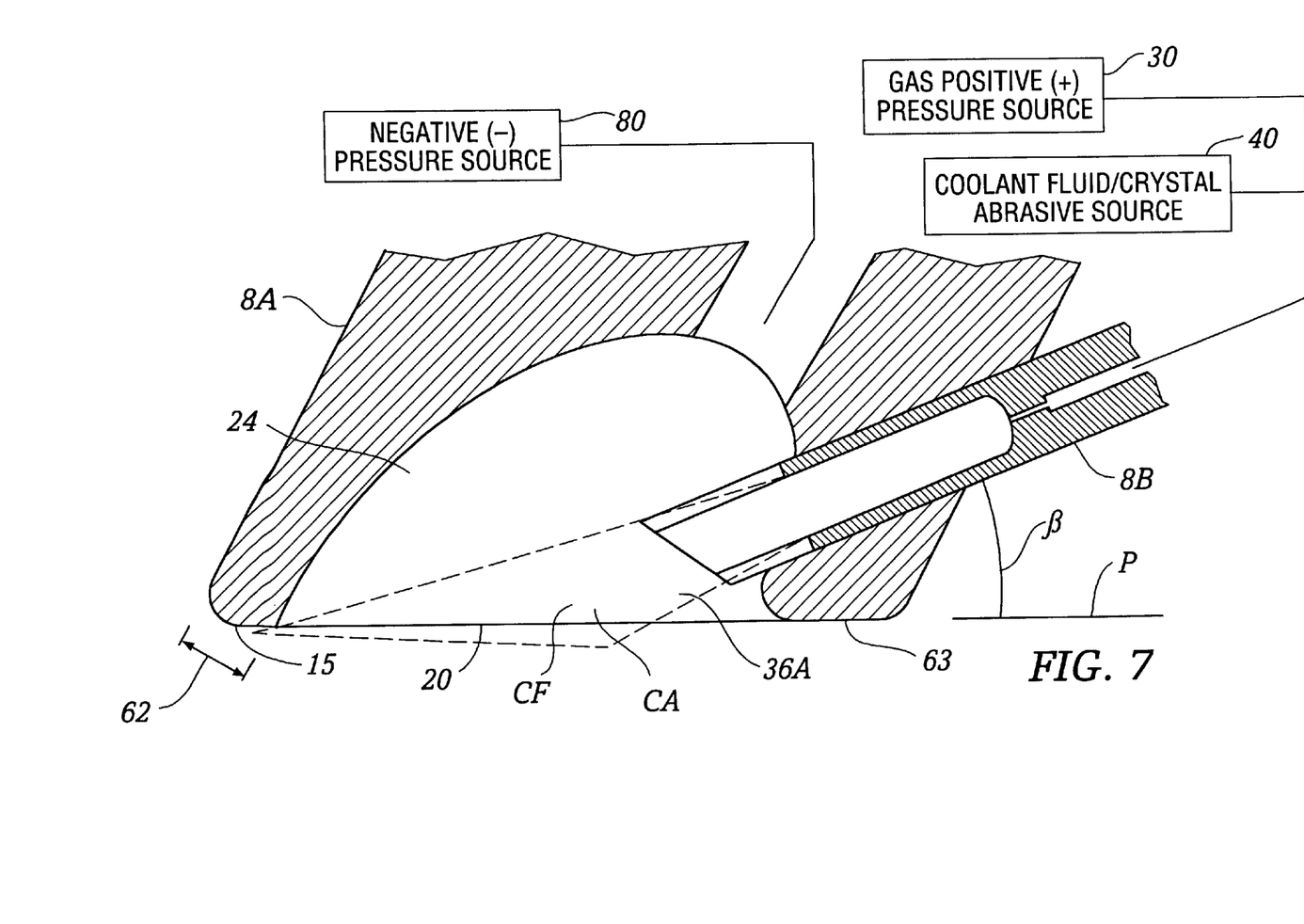
FIG. 7 is an enlarged view of the working end of the device of FIG. 2B.

FIG. 7 shows an enlarged sectional view of an open end portion of a body 8 (either body of FIGS. 2A–2B) with a skin-interface opening portion 22 surrounded by a surface area indicated at 15. Surface 15 around opening portion 22 preferably is smooth with a lubricious coating (e.g., Teflon® coating) to slide easily over the skin's surface. In this preferred embodiment, the body 8A is of any suitable transparent material, such as a transparent medical grade plastic. The transparency of body 8A will assist the operator in localizing treatment in a particular targeted skin treatment area. The transverse dimension of body 8A of FIGS. 2A–2B around opening portion 22 may vary from about 5.0 mm. to 50.0 mm. with a larger dimensioned body adapted for treating a larger skin area (e.g., arms, back, legs and décolletage). A typical dimension is from about 5.0 mm. to 15.0 mm. for a treatment area TA around a patient's face.

FIGS. 4 and 7 further shows exemplary ducts 44a–44b that have a minimal-dimension proximal jet portions 50a–50b and distal duct portions 54a–54b that are adapted to shape the gas flow streams therethrough and beyond as the gas streams 36A–36B spread into interior chamber 24. For this reason, FIG. 4 shows that the shape of ducts 44a–44b have length l and width w height dimension h in the distal duct portion thereof (54a–54b) which communicate with interior the chamber portion 24 proximate to opening 22. Preferably, the distal terminations 54a–54b of the ducts 44a–44b have a collective width w that may be defined angularly relative to opening 22 and collectively cover from about 45° to about 270° around opening 22 (see FIGS. 4 & 5A). The height dimension h of any distal termination 54a–54b of a duct 44a–44b preferably ranges from about 0.1 mm. to 4.0 mm. to provide means for spreading the air flow over a wider surface area and for creating an even distribution of fluid flow pressure over a treatment area TA of skin (see FIG. 8). Preferably, height dimension h ranges from about 0.5 mm. to 2.0 mm. The length l of any duct shown in FIG. 4 ranges from about 2.0 mm. to 15.0 mm. depending on the dimensions of opening 22 (see FIG. 4). Preferably, length l ranges from about 4.0 mm. to 10.0 mm. with such selected length having a significant effect on the velocity of the fluid flow in the treatment area TA. FIG. 4 further shows that jet portions 50a–50b preferably have a rectangular or elongate slit-type configuration but a pin-hole type aperture also may be suitable at the proximal end of each duct. These duct configurations and dimensions allow the hi-velocity gas streams 36A–36B to be flattened with an energy density spread evenly over the treatment area TA of the epidermis received by opening 22 (see FIG. 8). This aspect of the invention is an improvement over prior art devices that jet abrasives against the skin from a pin-hole jet that covered little surface area.

Figure 8:
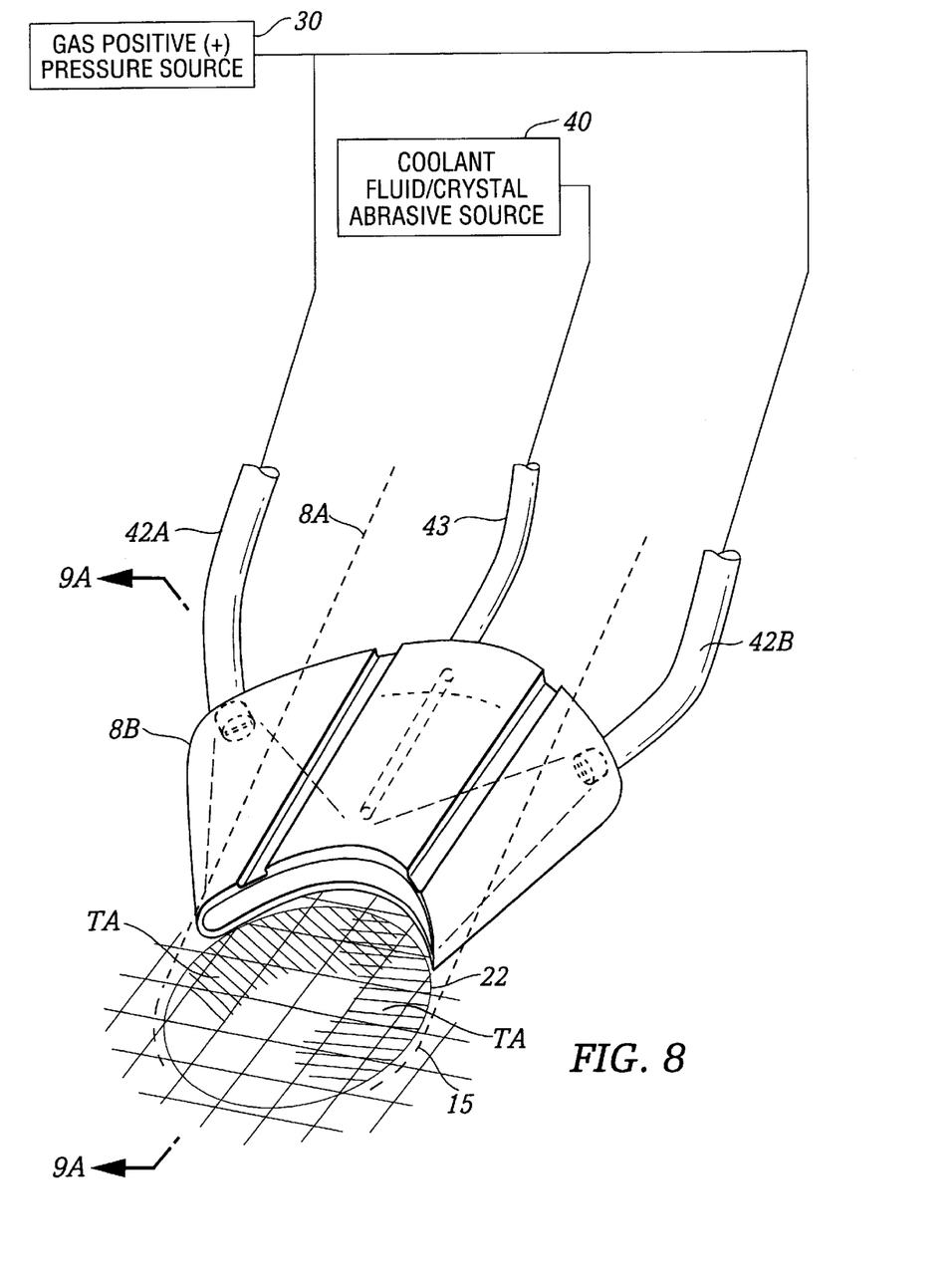
FIG. 8 is a view of the duct component of FIG. 4 showing an exemplary energy delivery pattern over a treatment area of a patient's skin.

FIG. 8 shows an exemplary duct component 8B that causes gas streams to be spread laterally to cover a wide treatment areas TA with an even energy distribution. The wide treatment TA area is allowed by both (or either, individually), (i) at least one laterally-distributed or flattened gas stream relative to its flow axis, and (ii) a plurality of partly overlapping gas streams to thus allow an even energy distribution within a scalable working end of the device. FIG. 8 shows an outline of opening 22 within face 15. The invention allows the dimensions of opening 22 to be in any shape and circumscribe an area ranging from about 5 mm. in diameter (or equivalent non-circular area) to about 40 mm. in diameter (or an equivalent non-circular area). FIG. 8 shows that opening 22 has a somewhat elliptical shape in the exemplary embodiment.

Figure 9A:
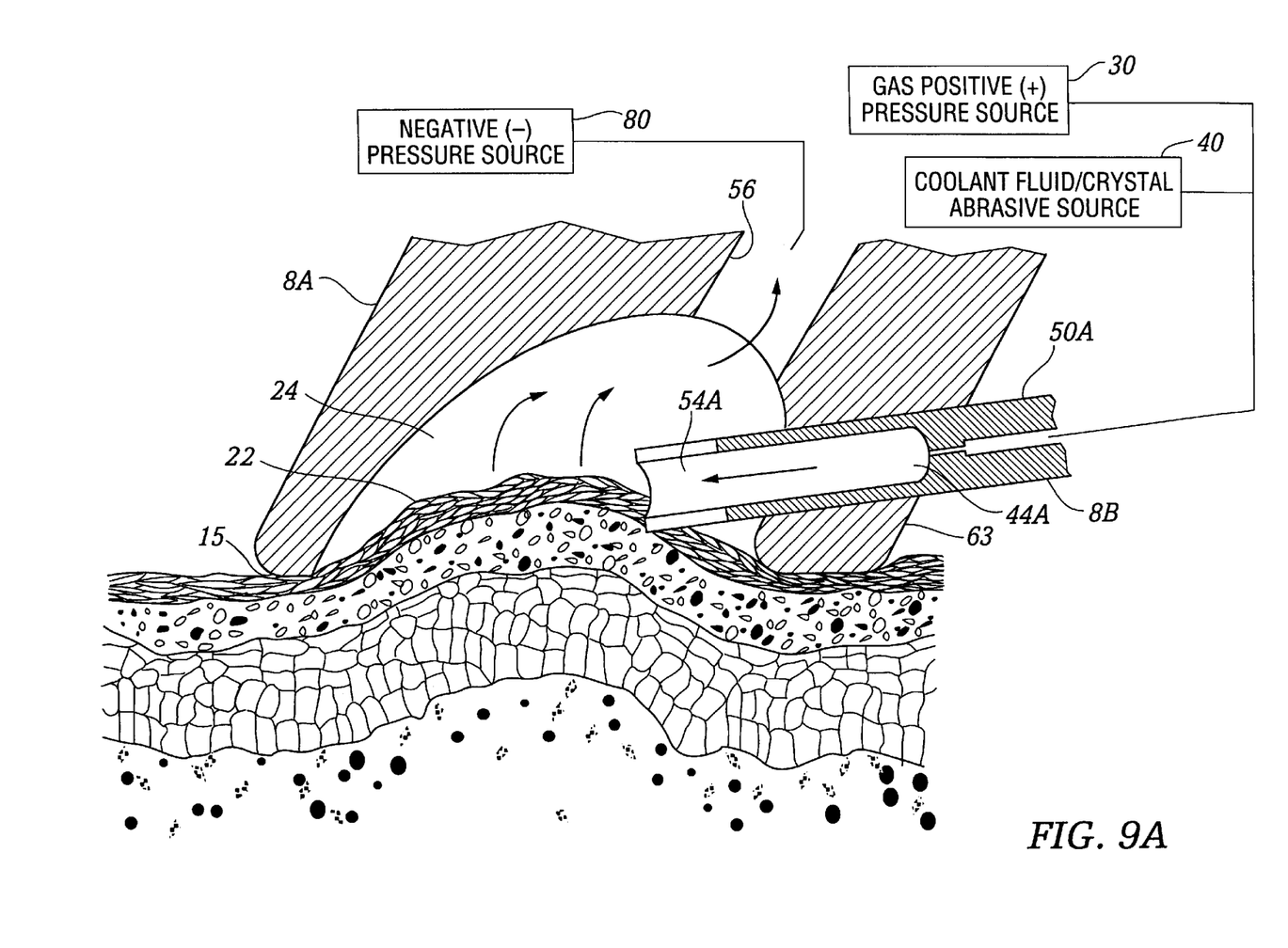
FIG. 9A showing a treatment area received by an opening portion in the working end of the device of FIG. 7 under aspiration pressures.
Figure 9B:
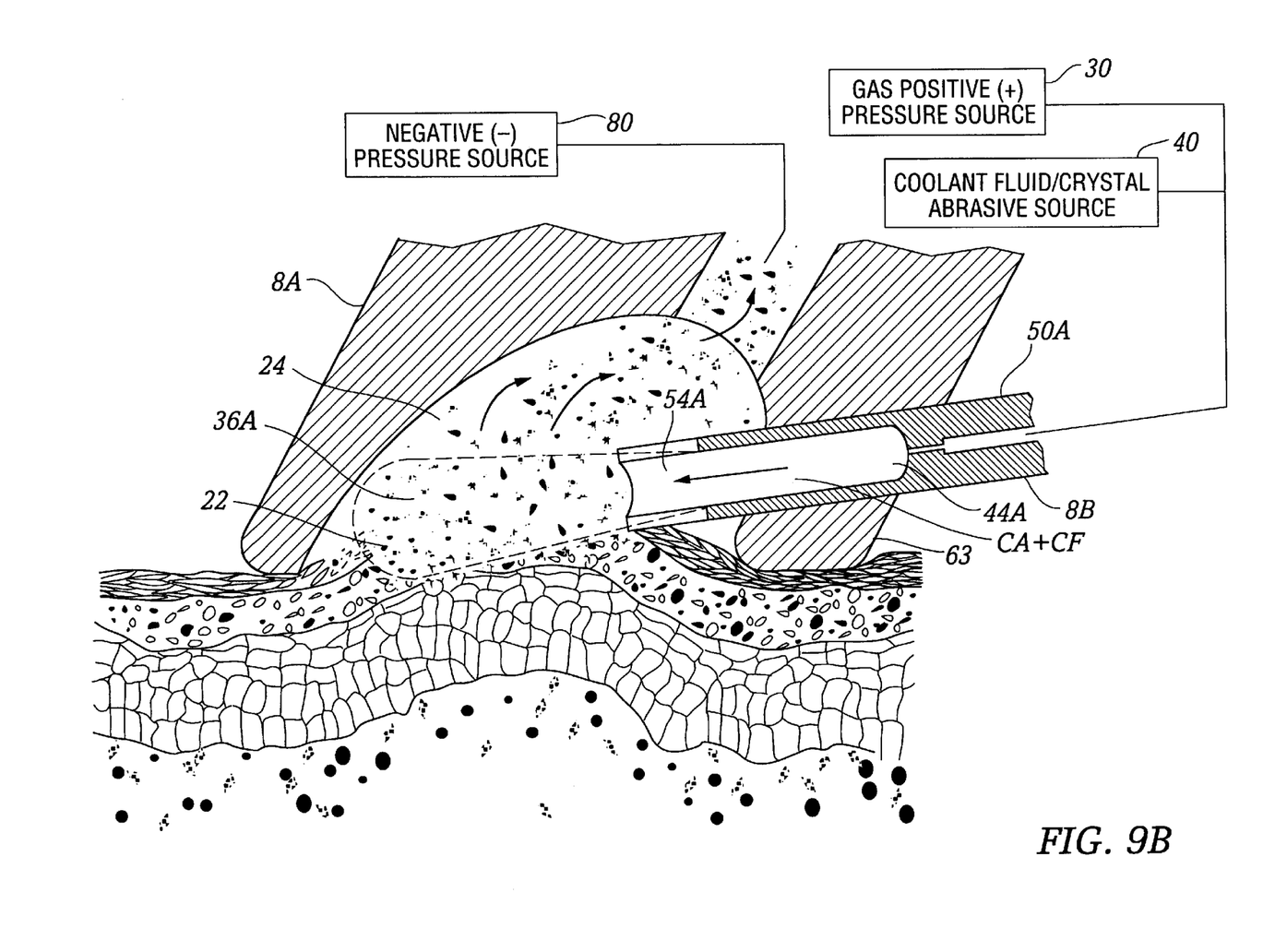
FIG. 9B depicting the skin being exfoliated in the treatment area by high-velocity gas flows and crystal abrasives.

As can be seen in FIGS. 3A–3B and FIG. 9A, body 8A defines interior chamber 24 therein that communicates with passageway 56 that is connected to a flexible aspiration tube 58 that extends to a remote collection reservoir 60. FIGS. 9A–9B show that opening 22 is adapted to partially receive the surface skin layers of a treatment area TA. The skin-interface surface 15 defines plane P and has a width dimension 62 that is sufficient to allow the face 15 to be supported on, and slide over, the skin's surface when negative pressurization exists in chamber 24. More particularly, the width dimension 62 of surface 15 ranges from about 1.0 mm. to 5.0 mm., and may be increased in width at heel portion 63.

Referring to FIGS. 9A–9B, interior chamber 24 of body 8A directly communicates with the two ducts 44a and 44b that are adapted to deliver a gas under pressure from $1^{st}$ delivery source 30 to interior chamber 24. The number of such ducts or passageways (i.e., 44a–44c) may range from one to about ten and fall within the scope of the invention. The term gas as used herein describes any suitable gas, but preferably is a medical grade $CO_2$ supplied in a pressurized tank for reasons described below. (It should be appreciated that compressed air also may be suitable; delivered either from a pressurized tank or a compressor). The system is adapted to provide gas inflow pressures from the $1^{st}$ delivery means 30 that range from about 5 psi to 125 psi on the proximal side of jet portions 50a–50c of any ducts in body component 8B.

Referring to FIG. 4 and FIGS. 9A–9B, the $2^{nd}$ delivery means 40 introduces the coolant fluid CF plus a crystalline agent CA into chamber 24 to intermix with the high-pressure gas streams 36A–36B provided by the $1^{st}$ delivery means, to thereafter impact the skin surface to abrade away superficial layers. A small diameter flexible supply tube 43 is best seen in FIG. 4 connected to bore 64 in body portion 8B. In FIG. 4, it can be seen that bore 64 is very small in diameter (e.g., 0.005" to 0.10" diameter). Preferably, the fluid CF plus agent CA is carried in a reservoir that may be pressurized or unpressurized. It has been found that the gas streams 36A–36B when passing the termination of bore 64 in interior chamber 24 is sufficient to draw the cooling fluid CF into the interior chamber. Optionally, the source or reservoir may be a pressurized vessel (or pressure source) fitted with a regulator 65 (not shown) as is known in the art to introduce a sterile fluid and crystalline agent into interior chamber 24. In such case, any sort of pump or pressure system may be used to supply fluid CF plus agent CA to the interior chamber 24 such as a peristaltic pump or another fluid pump type known in the art. To maintain a substantially uniform mixing of fluid CF plus abrasive CA, any mechanism known in the art may be used such as a vibratory mechanism. As indicated in FIG. 4, the system 5 may optionally have a thermal energy system 70 for altering the temperature of fluid CF to any temperature below the patient's body temperature, that is within a range from about 0° C. to about 38° C. Preferably, the temperature of the fluid CF is from about 0 ° C. to about 35° C. Still more preferred is a temperature range of fluid CF between about 5° C. to about 25° C. Any type of a thermal energy system 70 that is known in the art may be used to remove heat from (or apply heat to) the fluid CF, and a preferred system would use thermoelectric cooling (or heating) using bismuth telluride semiconductors in the manner commercialized by Melcor Corp., 1040 Spruce Street, Trenton, N.J. 08641A.

The coolant fluid CF is further provided with a selected amount of crystalline agent CA mixed therein, which may be any suitable crystalline substance such as aluminum oxide. The invention disclosed herein may be use with crystals ranging is size from about 1 $\mu$m to about 30 $\mu$m in maximum cross-sectional dimension. Preferably, the crystals are from about 5 $\mu$m to about 15 $\mu$m in maximum cross-sectional dimension to allow a very fine abrasion of the epidermis. The use of such fine crystals was not feasible with prior art equipment for two reasons: First, such fine crystals would cause too much pain to the patient, which aspect of the prior art is overcome by the cooling system of the present invention. Second, such fine crystals would cause a greater health hazard if inhaled by the patient or operator since they could be absorbed in the patient's or operator's lungs. As described above, the spent fluid adheres to the crystals allowing the fluid CF and crystals CA, together with skin debris, to be easily collected and aspirated into the collection reservoir for disposal.

The negative (−) pressurization means or vacuum source 80 is provided which communicates with interior chamber 24 in body 8A for evacuating skin debris and spent fluid CF plus agent CA from the treatment site TA. As can be seen in FIGS. 3A–3B and 9A–9B, flexible tube 58 extends from interior chamber 24 to a collection reservoir 60. The negative (−) pressurization source 80 may be any suitable vacuum source known in the art. Between the negative pressurization source 80 and remote collection reservoir 60 is a filter 84 subsystem that is known in the art for collecting aspirated fluid CF plus agent CA and skin detritus that is captured by the negative pressure in chamber 24. The collection reservoir 60 and filter 84 are of inexpensive plastic and other materials that are disposable.

FIGS. 2A–2B illustrate that the negative (−) pressurization source 80 and the $1^{st}$ and $2^{nd}$ delivery means 30 and 40 are provided with adjustable valve means 85a, 85b and 85c for adjusting the pressure level setting, and balance between, the various fluid delivery sources and the negative (−) pressurization source 80. The physician will learn from experience how to balance the pressure levels from the cooperating pressurization sources to jet chemical agents and collect such spent agents without suctioning skin too tightly against the treatment areas TA. In a preferred embodiment, the computer controller 25 will be provided with algorithms to automatically balance fluid flow pressures and aspiration pressures, as well as with algorithms for any dimensions of ducts within component 8B.

A trigger or switch component 88 is provided for sequentially (or otherwise) actuating the $1^{st}$ and $2^{nd}$ delivery means or sources 30 and 40, and the negative (−) pressurization source 80. In general, the trigger mechanism 88 (handswitch or footswitch) has a repose OFF position and a $1^{st}$ ON position and a $2^{nd}$ ON position. The $1^{st}$ position actuates the $1^{st}$ delivery means 30 and negative pressure source 80 to thereby jet gases through the interior chamber and aspirate the gases. The $2^{nd}$ ON position of the trigger 88 actuates the $2^{nd}$ delivery means 40 to deliver cooling fluid CF and crystal agent CA into the gas streams 36A–36B and against the patient's skin while still actuating the $1^{st}$ and $2^{nd}$ delivery means. The trigger mechanism 88 preferably is differently sequentially timed (i) when moving the switch to the $2^{nd}$ On position from the OFF position, and (ii) when moving the switch from the $2^{nd}$ ON position to the OFF position similar to manner described in patent application Ser. No. 09/271,610 filed Mar. 17, 1999 titled Technique and System for Controlled Chemically-Mediated Removal of Skin Layers.

2. Method of Use of Type "A" Embodiment.

The method for utilizing the system 5 to controllably or remove superficial layers of a patient's epidermis can be described briefly as follows (see FIGS. 9A–9B). A fluid CF is selected and the controller 25 of system 5 is programmed to maintain the fluid CF at a particular temperature. The fluid is also selected to carry a particular dimension (or grit) of abrasive crystal CA.

Next, referring to FIG. 9A, the operator (after cleansing the patient's skin) places the surface 15 of body 8A on the patient's skin and moves the trigger mechanism 88 to a $1^{st}$ position thereby actuating the negative (−) pressure source 80 to draw the tissue surface against or into opening 22. At the same time, or a selected interval later, the switch actuates the $1^{st}$ delivery means 30 to cause $CO_2$ gas (or another gas) to be jetted through apertures 50a–50b and ducts 44a–44b into interior chamber 24. Thus, the negative (−) pressure source 80 captures and aspirates the gas stream 36A–36B of the $1^{st}$ delivery means 40 after the gas stream strikes the skin surface in the interior chamber 24. It is believed that only an independent and computer-controlled aspiration pressure source 80 will allow the use of large diameter openings 22 in the working end of body 8 to substantially draw the skin upward into the opening 22 to thus allow the wide paths of treatment described above.

The operator then moves the trigger mechanism 88 to a $2^{nd}$ position that actuates the $2^{nd}$ fluid delivery means 40 to allow low-pressure or no pressure flow of cooling fluid CF and crystalline agent CA into interior chamber to mix with high-velocity gas streams 36A and 36B as shown in FIG. 9B. (The flow of fluid CF and crystalline agent CA optionally may be triggered automatically a pre-selected time interval after the movement of the trigger to the $1^{st}$ position). The mixing of the crystalline agent CA with the high-velocity air streams proves to be an economical and efficient manner to cause a fine abrasion of the epidermis. Further, the flow of atomized fluid cools the skin as described above which reduces or eliminates the sensation of pain. As can be seen in FIG. 9B, the negative (−) pressure source aspirates the spent fluids and skin detritus from the interior chamber 24. By moving the trigger from the $2^{nd}$ position back to the $1^{st}$ position, operator can instantly terminate the low pressure flow of fluid CF and crystal CA to stop the flow of cooling fluid CF and crystalline agent CA so to prevent contamination of the environment when body 8 is removed from the patient's skin.

While maintaining the trigger mechanism in the $2^{nd}$ position, the operator then sweeps the working face 15 over the patient's skin to exfoliate a path therein. At the end of a sweep, the operator releases the trigger 88 which in sequence terminates the $2^{nd}$ delivery means 40, then the $1^{st}$ delivery means and then a slight time interval later terminates the negative (−) pressure source 80 to allow the operator to easily lift the body from the patient's skin. The exfoliated path can be seen and the operator then can exfoliate another slightly overlapping or adjacent path by repeating the above steps until exfoliation is completed over the treatment area.

The system 5 of the invention is commercialized as a kit with instructions for use that include the following. The steps in the instructions first explain to select a desired temperature of cooling fluid CF for a particular dermabrasion, and to select a particular grit size of crystal abrasive CA. The instructions further explain to select a particular pressure for gas inflows from $1^{st}$ delivery means ranging from about 5 psi to 125 psi. The instructions further explain to select a particular negative pressure for aspiration of spent fluids and skin debris from the interior chamber 24. The instructions then direct the operator (after cleansing the patient's skin) to press the surface 15 of the body 8A on the skin of the patient in the treatment area TA. The instructions for operating the system then direct the operator to actuate the trigger mechanism 88 to a $1^{st}$ position to cause the high velocity gas streams to be jetted against the skin by the $1^{st}$ delivery means, while at the same time the negative (−) pressure source 80 is activated to aspirate debris from chamber 24 into the collection reservoir. The operating instructions further direct the operator to thereafter move the trigger to a $2^{nd}$ position to actuate the low-pressure cooling fluid and crystalline agent delivery means 40, and to sweep the working face 15 over the patient's skin to abrade the epidermis in a path. At the end of a sweep, the operator is instructed to release the trigger to the release position to terminate fluid flows, that is cooling fluid CF and crystalline agent CA and the high velocity gas streams, and negative pressure in sequence to allow lifting of the body from the patient's skin. The operating instructions further direct the operator to repeat the above steps to abrade superficial layers in slightly overlapping or adjacent paths to controllably remove superficial layers in the treatment area. The instructions then direct the operator to dispose of the aspirated and collected skin detritus and spent fluids and crystalline agent.

Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A system for abrading of a surface layer of a patient's skin, comprising:
   (a) a hand-held body having a working face with an opening portion therein that communicates with an interior chamber portion of the body;
   (b) at least one fluid-flow duct terminating in said interior chamber about the opening portion for delivering at least one high-velocity gas stream;
   (c) at least one fluid-flow bore terminating proximate to said fluid-flow duct and said interior chamber for delivering a cooling fluid;
   (d) a pressure source operatively connected to said at least one duct for delivering said at least one high-velocity gas stream;
   (e) a cooling fluid source operatively connected to said at least one fluid-flow bore; and
   (f) a negative pressurization source operatively connected to said interior chamber.

2. The system of claim 1 wherein the cooling fluid has a temperature ranging between about 0° C. to 35° C.

3. The system of claim 1 wherein the cooling fluid has a temperature ranging between about 5° C. to 20° C.

4. A method of removal of epidermis with a hand-held body having a open end portion communicating with an interior chamber that carries a gas pressure source and at least one duct for jetting a gas into the interior chamber and sources for introducing a cooling fluid and abrasive crystals into the interior chamber, together with a negative pressurization means for aspirating skin detritus from the interior chamber, comprising the steps of:

(a) placing the open end portion of the body over the skin of a patient;

(b) actuating the negative pressurization means thereby drawing the skin against the open end portion; and (c) contemporaneous with, or at a selected time interval after step (b), actuating the gas pressure source to produce at least one high-velocity gaseous stream proximate to a surface of the skin interfaced with said open end portion;

(d) contemporaneous with, or at a selected time interval after step (c), introducing coolant fluid and crystals into the at least one gaseous stream and against the skin interfaced with said open end portion, wherein the fluid cools the skin and the high-velocity gaseous streams and the crystals abrade and remove a surface layer of skin.

5. The method of claim 4, further comprising the step of sweeping the open end portion over the skin thereby controllably removing said surface layer of skin in a path.

6. The method of claim 4, further comprising the step of allowing the negative pressurization means to aspirate removed skin debris and spent gases and fluids from the treatment site.

7. The method of claim 6, further comprising the step of aspirating said skin detritus and spent gases and fluids to a remote collection reservoir.

8. A dermal treatment system comprising:

a delivery device comprising a skin-contacting surface defining a treatment region, a dermal treatment medium entrance port and an exhaust port, the entrance and exhaust ports opening into the treatment region;

first and second flowable dermal treatment media sources selectively fluidly coupled to the entrance port so to provide dermal treatment media to the treatment region for contact and interaction with a patient's skin;

at least one of the first and second media sources comprising a coolant fluid;

at least one of the first and second media sources also comprising a fluid carrying flowable particles; and a vacuum system operably coupled to the exhaust port so to withdraw dermal treatment media and any removed dermal tissue from the treatment region.

9. The system according to claim 8 wherein said delivery device comprises a hand-held housing.

10. The system according to claim 9 wherein the housing is an elongate housing with the skin-contacting surface at one end thereof.

11. The system according to claim 9 wherein the housing is a generally cup-shaped housing.

12. The system according to claim 8 wherein the entrance port comprises first and second subports spaced apart from one another and fluidly coupled to the first and second media sources, respectively.

13. The system according to claim 12 wherein:

the coolant fluid comprises a liquid coolant;

the fluid carrying the flowable particles is the liquid coolant;

the first media source comprises the liquid coolant carrying the flowable particles and the second media source comprises a pressurized gas;

the liquid coolant carrying the fluid particles is flowable through the first subport at a first rate chosen so that upon entry into the treatment region the liquid coolant carrying the fluid particles is at a first chosen rate; and the pressurized gas is flowable through the second subport at a second rate chosen so that upon entry into the treatment region the pressurized gas is flowing at a second chosen rate.

14. The system according to claim 8 wherein the entrance port comprises first, second and third subports, the subports being spaced apart from and at angles to one another, the first subport fluidly coupled to the first media source and the second and third subports fluidly coupled to the second media source.

15. The system according to claim 8 wherein the coolant fluid is a liquid.

16. The system according to claim 15 wherein the first media source comprises the flowable particles.

17. The system according to claim 15 wherein the liquid is at a temperature of about 0° C. to 35° C.

18. The system according to claim 8 wherein the flowable particles have a maximum cross-sectional dimension of no more than about 30 microns.

19. A dermal treatment system comprising:

a delivery device comprising a skin-contacting surface defining a treatment region, first and second dermal treatment media entrance ports and an exhaust port, the entrance ports and the exhaust port opening into the treatment region, the entrance ports being spaced apart from and at an angle to one another;

a first flowable dermal treatment media source, comprising an abrasive coolant liquid, selectively fluidly coupled to the first entrance port so to provide coolant liquid containing solid abrasive particles to the treatment region for contact and interaction with a patient's skin;

a second flowable dermal treatment media source, comprising a gas, selectively fluidly coupled to the second entrance port so to provide pressurized gas to the treatment region for contact and interaction with a patient's skin; and a vacuum system operably coupled to the exhaust port so to withdraw dermal treatment media and any removed dermal tissue from the treatment region.

20. A method for treating the skin surface of a patient comprising:

placing a treatment device against a patient's skin creating a treatment region at a skin treatment site;

directing a first dermal treatment medium, comprising a coolant fluid, through a first port and into the treatment region for contact with the skin treatment site;

directing a second dermal treatment medium, comprising a pressurized gas, through a second port and into the treatment region for contact with the skin treatment site, at least one of the first and second dermal treatment media comprising a flowable abrasive; and vacuum exhausting dermal treatment media and any removed dermal tissue from the treatment region.

21. The method according to claim 20 wherein the placing step includes moving the treatment device over the surface of the patient's skin.

22. The method according to claim 20 wherein the second dermal treatment medium directing step directs treatment media through first and second subports of said second port and along intersecting paths.

23. The method according to claim 20 wherein the first dermal treatment medium directing step is carried out with the first dermal treatment medium comprising a coolant liquid and the flowable abrasive.

24. The method according to claim 20 wherein the first and second dermal treatment media directing steps are carried out so that the first and second dermal treatment media flow within the treatment region along intersecting paths.

25. The method according to claim 20 wherein at least one of the directing steps is carried out with the dermal treatment medium of said at least one of the directing steps entering the treatment region at an angle of about 0° to 40° to the patient's skin.

26. The method according to claim 20 wherein at least one of the directing steps is carried out with the dermal treatment medium of said at least one of the directing steps entering the treatment region at an angle of about 5° to 25° to the patient's skin.

27. The method according to claim 20 wherein the first dermal treatment medium directing step is carried out using a liquid as the coolant fluid, and further comprising the step of cooling the liquid to about 0° C. to 35° C.

28. The method according to claim 20 wherein the first dermal treatment medium directing step is carried out using a liquid as the coolant fluid, and further comprising the step of cooling the liquid to about 5° C. to 25° C.

29. The method according to claim 20 wherein the second directing step occurs during the first directing step.

30. A method for treating the skin surface of a patient comprising:

positioning a treatment device against a patient's skin creating a treatment region at a skin treatment site, the treatment device comprising first and second media entrance ports;

directing a first flowable dermal treatment medium, comprising a pressurized abrasive coolant liquid, through the first entrance port and into the treatment region for contact with the skin treatment site;

directing a second dermal treatment medium, comprising a pressurized gas, through the second entrance port and into the treatment region for contact with the skin treatment site, the directing steps being carried out along generally intersecting paths; and vacuum exhausting dermal treatment media and any removed dermal tissue from the treatment region.

31. A method for treating the skin surface of a patient, comprising:

positioning an abrasive-carrying treatment device against a patient's skin creating a treatment region at a skin treatment site, the treatment device comprising a media entrance port, wherein a treatment medium is delivered under pressure through the media entrance port, and wherein the treatment medium comprises a cooling liquid;

translating the treatment device over the skin treatment site whereby the abrasive and the cooling liquid removes and transports dermal tissue; and vacuum exhausting at least a portion of the treatment medium and removed dermal tissue from the treatment region.

32. The method of claim 31 further comprising the step of supplying the cooling liquid at a temperature of 0° and 35° C.

* * * * *